United States Patent [19]

Ockuly et al.

[11] Patent Number: 5,879,296
[45] Date of Patent: Mar. 9, 1999

[54] GUIDING INTRODUCERS FOR USE IN THE TREATMENT OF LEFT VENTRICULAR TACHYCARDIA

[75] Inventors: John D. Ockuly, Minnetonka; James A. Hassett, Bloomington, both of Minn.

[73] Assignee: Daig Corporation, Minnetonka, Minn.

[21] Appl. No.: 800,287

[22] Filed: Feb. 12, 1997

Related U.S. Application Data

[63] Continuation of Ser. No. 389,252, Feb. 16, 1995, Pat. No. 5,722,400, Continuation-in-part of Ser. No. 146,744, Nov. 3, 1993, Pat. No. 5,427,119.

[51] Int. Cl.$^6$ .............................. A61B 5/04; A61B 17/39; A61N 1/05
[52] U.S. Cl. .............................. 600/374; 604/281; 606/41
[58] Field of Search .......................... 600/374; 607/122; 606/41; 604/280, 281

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,641,649 | 2/1987 | Walinsky et al. . |
| 4,882,777 | 11/1989 | Narwa . |
| 4,883,058 | 11/1989 | Ruiz . |
| 4,898,591 | 2/1990 | Jang et al. . |
| 4,945,912 | 8/1990 | Langberg . |
| 5,016,640 | 5/1991 | Ruiz . |
| 5,172,699 | 12/1992 | Svenson et al. . |
| 5,215,540 | 6/1993 | Anderhub . |
| 5,222,501 | 6/1993 | Idekar et al. . |
| 5,231,994 | 8/1993 | Harmjanz . |
| 5,242,441 | 9/1993 | Avitall . |
| 5,476,495 | 12/1995 | Kordis et al. ........................ 607/122 |

OTHER PUBLICATIONS

Singer, I et al. "Catheter Ablation For Arrhythmias", Clinical Manual of Electrophysiology, pp. 421–431 (1993).
Falk, R.H. et al. "Atrial Fibrillation Mechanisms and Management," pp. 359–374 (1992).
Horowitz, L.N. "Current Management of Arrhythmias," pp. 373–378 (1991).
Gallagher, J.J. et al. "Catheter Technique For Closed Chest Ablation of the Atrioventricular Conduction System" N. Engl. J. Med., vol. 306, pp. 194–200 (1982).
Tracy, L.M. "Radiofrequency Catheter Ablation of Ectopic Atrial Tachy–Cardia Using Paced Activation Sequence Mapping" J. Am. Coll. Cardiol., vol. 21, pp. 910–917 (1993).
Saul, J.P. et al. "Catheter Ablation of Accessory Atrioventricular Path–ways in Young Patients: Use of Long Vascular Sheaths, the Transseptal Approach and a Retrograde Left Pasterior Parallel Approach" J. Amer. Coll. Card., vol. 21, No. 3, pp. 571–583 (1993).
Swartz, J.F. et al. "Radiofrequency Endocardial Catheter Ablation of Accessory Atrioventricular Pathway Atrial Insertion Sites" Circulation, vol. 87, No. 2, pp. 487–499 (1993).
USCI Positrol II & Nycore Cardiovascular Catheters (604/281), 1990.

*Primary Examiner*—Lee Cohen
*Attorney, Agent, or Firm*—Scott R. Cox

[57] ABSTRACT

A process for the treatment of ventricular tachycardia in the left ventricle using a retrograde approach by use of ablation and/or mapping catheters guided by precurved guiding introducers. Also disclosed are predetermined shapes for the guiding introducers to be used for the treatment of ventricular tachycardia in the left ventricle using a retrograde approach.

8 Claims, 6 Drawing Sheets

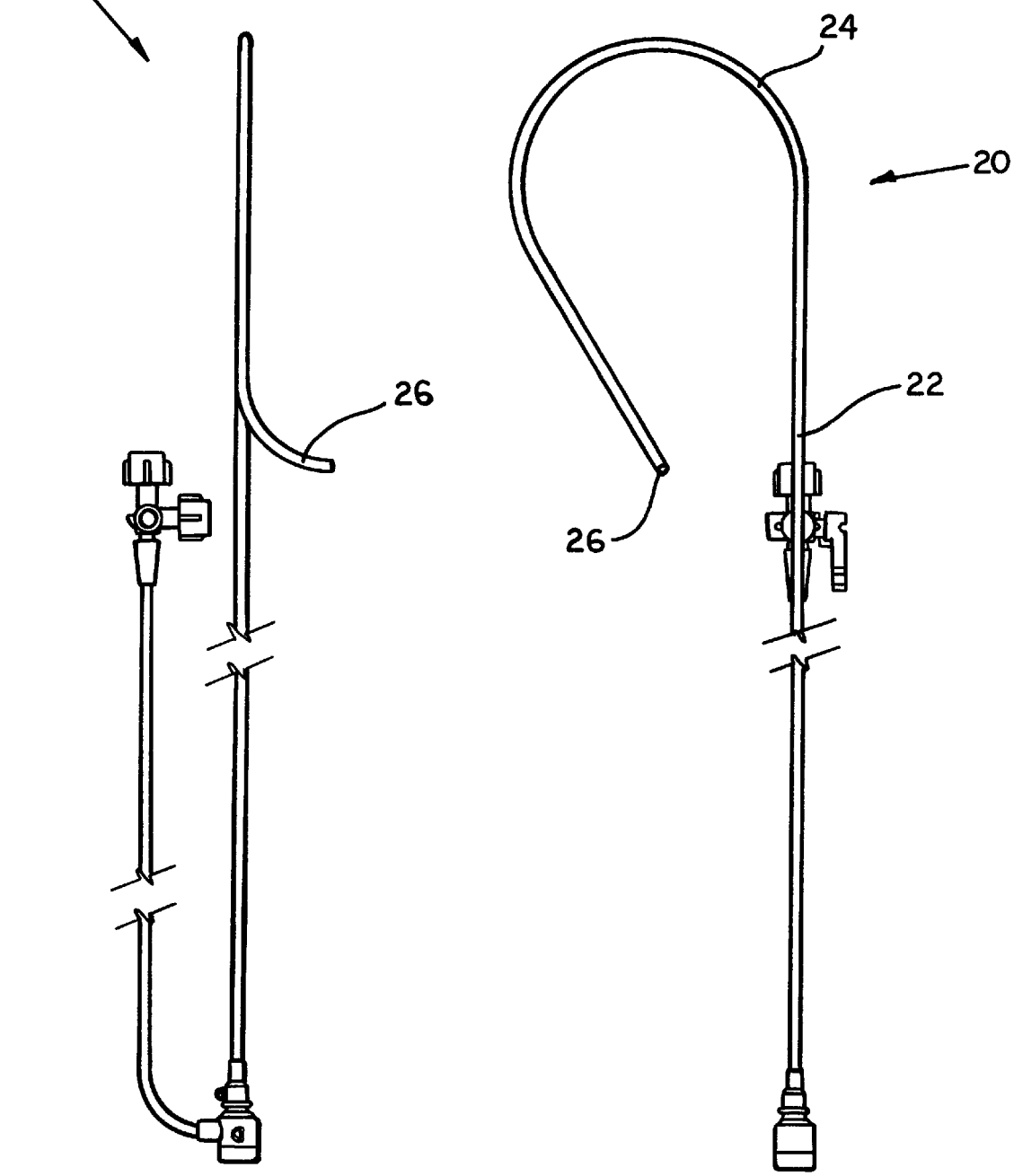

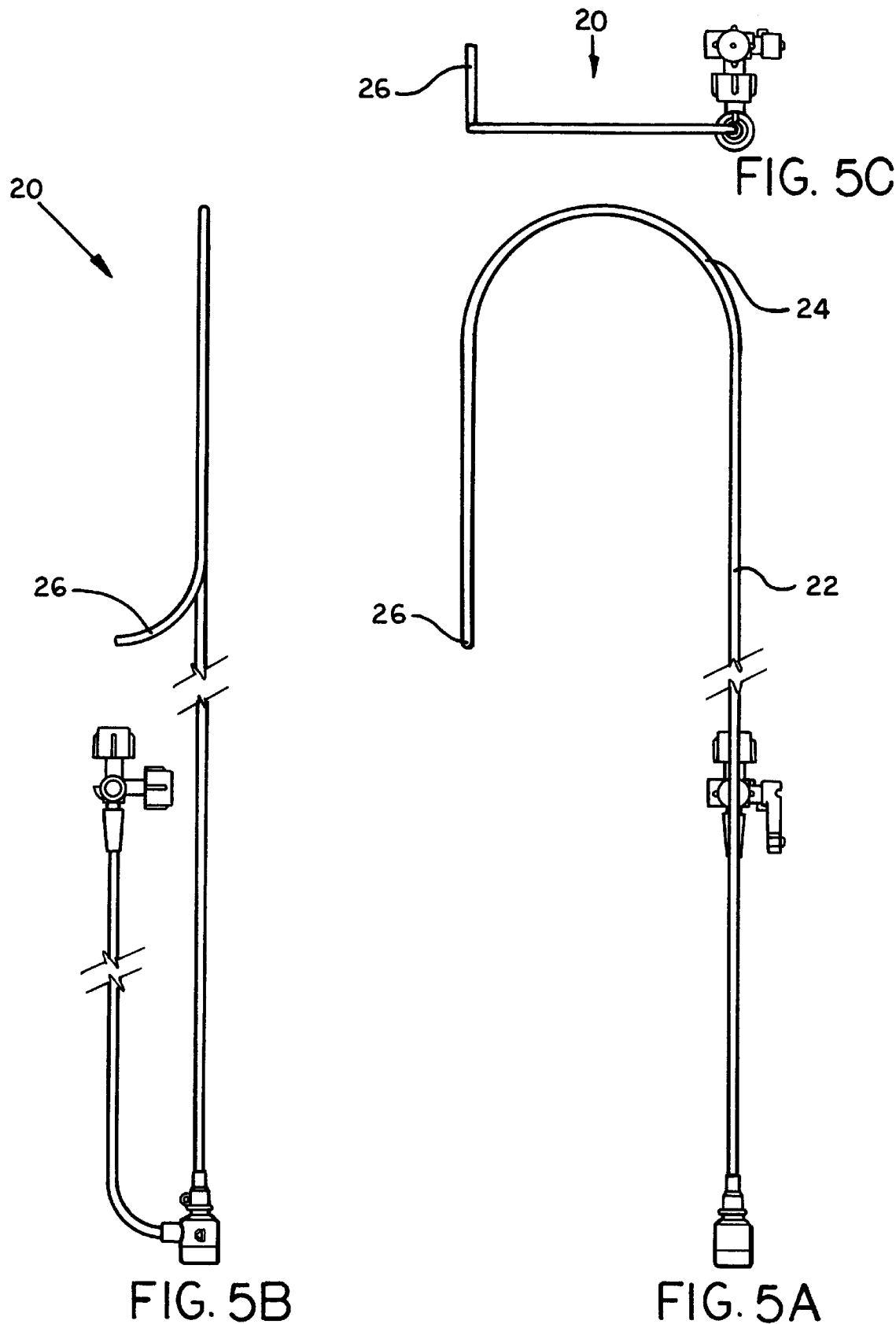

5,879,296

GUIDING INTRODUCERS FOR USE IN THE TREATMENT OF LEFT VENTRICULAR TACHYCARDIA

This application is a continuation of Ser. No. 08/389,252, filed Feb. 16, 1995, now U.S. Pat. No. 5,722,400, which was a continuation-in-part of application Ser. No. 08/146,744, filed Nov. 3, 1993, now U.S. Pat. No. 5,427,119.

BACKGROUND OF INVENTION

1. Field of Invention

This invention relates to introducers. More particularly, this invention relates to guiding introducers of specific shapes for use within the left ventricle of the human heart for the treatment of left ventricular tachycardia.

2. Prior Art

Introducers and catheters have been in use for medical procedures for many years. For example, one use has been to convey an electrical stimulus to a selected location within the human body. Another use is to monitor and make measurements for diagnostic tests within the human body. Catheters may be used by a physician to examine, diagnose and treat while positioned at a specific location within the body which is otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters. Thus, there are a number of references which disclose catheters with predetermined shapes, designed for use during specific medical procedures generally associated with the heart or the vascular system. Because of precise physiology of the heart and the vascular system, catheters or introducers with precisely designed shapes for predetermined uses within the human heart and vascular system are increasingly important.

Catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

U.S. Pat. No. 4,641,649 discloses the use of high frequency energy for the treatment of tachycardia or cardiac dysrhythmia. See also U.S. Pat. Nos. 5,246,438 and 4,945,912 for the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, U.S. Pat. No. 5,172,699 discloses a general process for the identification and ablation of ventricular tachycardia sites. See also U.S. Pat. Nos. 5,222,501 and 5,242,441.

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation 87:487–499 (1993). See also Tracey, C. N. "Radio Frequency Catheter Ablation of Ectopic Atrial Tachycardia Using Paced Activation Sequence Mapping" J. Am. Coll. Cardiol. 21:910–917 (1993).

Accordingly, it is an object of this invention to prepare a guiding introducer for selected medical procedures in the left ventricle.

It is a further object of this invention to prepare a guiding introducer for use in selected electrophysiology procedures within the left ventricle of the heart.

Another object of this invention is to prepare a guiding introducer for use in selected ablation procedures within the left ventricle of the heart.

It is a still further object of this invention to prepare a guiding introducer for use in the selected ablation of sites in the left ventricle of the heart for the treatment of left ventricular tachycardia.

These and other objects are obtained by the design of the guiding introducers disclosed in the instant invention.

SUMMARY OF INVENTION

The instant invention includes a process for the treatment of ventricular tachycardia within the left ventricle of the heart comprising (a) introducing into the left ventricle a precurved, guiding introducer, wherein said guiding introducer contains a lumen running lengthwise therethrough, a proximal and a distal end and wherein the introducer is comprised of shaped first, second and third sections;

(b) introducing into the lumen of the guiding introducer an ablation and/or mapping catheter containing a proximal and distal end, wherein said catheter has one or more electrodes located at or near the distal end of the catheter;

(c) guiding the catheter to a selected location within the left ventricle by use of the guiding introducer; and (d) mapping and/or ablating the selected location within the left ventricle by use of the electrodes of the catheter.

In addition, the instant invention is a guiding introducer to be used in the left ventricle for treatment of ventricular tachycardia comprising a first, second and third sections.

BRIEF DESCRIPTION OF THE DRAWINGS

FIG. 3A is a side view of the second embodiment of the guiding introducer for treatment of ventricular tachycardia, wherein the site for treatment in the left ventricle is on the anterior freewall, such that the side port tubing attached to the proximal end of the guiding introducer is located directly behind the first section of the guiding introducer.

FIG. 3B is a side view of the second embodiment of the guiding introducer rotated 90° clockwise from the position of FIG. 3A, when viewed from the perspective of the proximal end of the guiding introducer, such that the side port is directed to the left of the guiding introducer.

FIG. 3C is a top view of the second embodiment of the guiding introducer rotated 90° upward from the position of FIG. 3A, such that the side port is directed upward from the first section of the guiding introducer.

FIG. 5A is a side view of the fourth embodiment of the guiding introducer for treatment of ventricular tachycardia where the site for treatment in the left ventricle is on the posterior freewall, such that the side port tubing attached to the proximal end of the guiding introducer is located directly behind the first section of the guiding introducer.

FIG. 5B is a side view of the fourth embodiment of the guiding introducer rotated 90° counterclockwise from the position of FIG. 5A, when viewed from the perspective of the proximal end of the guiding introducer, such that the side port is directed to the left of the guiding introducer.

FIG. 5C is a top view of the fourth embodiment of the guiding introducer rotated 90° upward from the position of FIG. 5A such that the side port is directed upward from the guiding introducer.

DESCRIPTION OF THE INVENTION

Figure 1A:
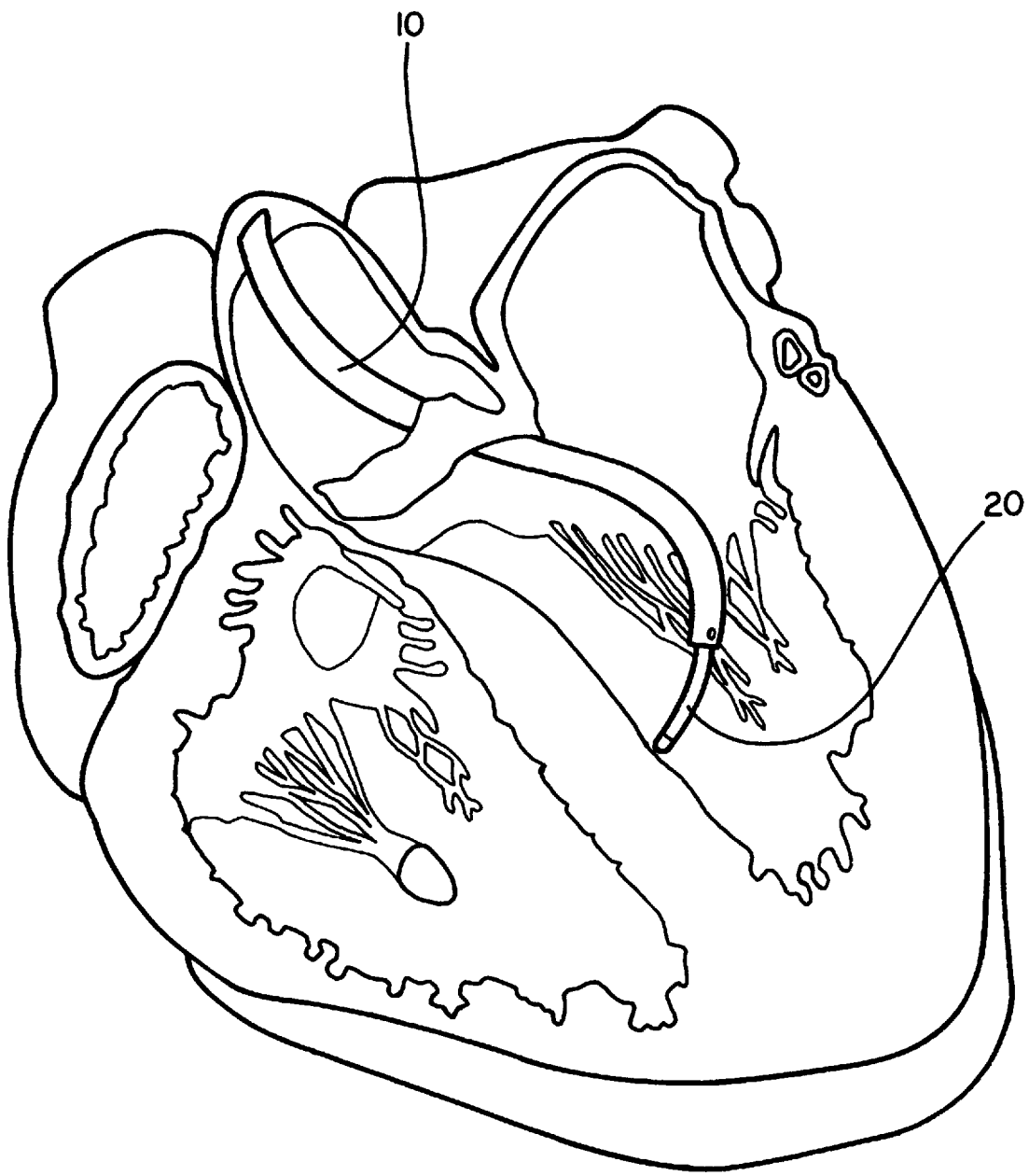
FIG. 1A is a cut away view of the heart showing a retrograde guiding introducer supporting a catheter for ablation procedures on the left ventricular septal wall.

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. The mitral valve contained within the atrioventricular septum communicates the left atrium with the left ventricle. On the inner wall of the right atrium, where it is connected with the left atrium, is a recessed portion, the fossa ovalis. Between the fossa ovalis and the tricuspid valve is the opening or ostium for the coronary sinus. The coronary sinus is a large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome have an arrhythmia, the cause of which is believed to be the existence of an anomalous conduction pathway or pathways that connect the atrial muscle tissue directly to the ventricular muscle tissue, thus by-passing the normal His-Purkinje system. These pathways are usually located in the fibrous tissue that connect the atrium and the ventricle.

Another arrhythmia is ventricular tachycardia ("V.T."). VT is a disease of the heart in which the heart's normal arrhythmic contraction is altered. Frequently, the rate of heart beat is too fast although the conditions of the disease itself are generally quite complex. VT occurs most often in patients following a myocardial infarction. A myocardial infarction, commonly referred to as a heart attack, is a loss of blood to a region of the heart causing the myocardial tissue in that region to die and be replaced by an area of scar tissue known as a myocardial infarct. Frequently, the myocardial infarct is present in the left ventricle.

As a result of the myocardial infarct, circular pathways ("reentry circuits") are frequently created within the left ventricle for the conduction of the electrical impulses of the heart. These reentry circuits cause the electrical impulses of the heart to travel in circles about the myocardial infarct, frequently causing an erratic and sometimes accelerated beating of the heart. These reentry circuits may also occur around discreet elements of the heart, such as valves. In addition, the reentry circuits sometime occur around both the myocardial infarct and the discreet elements of the heart.

In the past VT has been treated by the use of drugs such as lidocaine, quinidine and procainamide. More recently, beta-blocking drugs have been used for its treatment. In cases where drug therapy has been ineffective, surgical procedures have been used to excise the tissue causing the arrhythmia. The procedure involves the removal of a portion of the heart muscle, particularly that portion around which the reentry circuit has formed. By the excision of this portion of the heart muscle, scar tissue is formed which prevents the reformation of the reentry circuit. Obviously such procedures are high risk, frequently requiring prolonged periods of hospitalization and recuperation. As an alternative to these procedures, ablation devices have been used for the diagnosis and treatment of cardiac arrhythmias including, specifically, VT. See, for example, U.S. Pat. No. 5,222,501.

Ablation procedures, however, are frequently unsuccessful unless repeated many times. It is presumed that one reason for the difficulty of ablation of ventricular tissue for the treatment of VT is the failure to destroy completely the reentry circuit in the ventricular tissue because of the inherent thickness of the ventricular tissue and the size of the reentry circuit itself. To effectively ablate the ventricular tissue, the ablation catheter must be positioned precisely within the ventricle and maintained in contact with the ventricular tissue throughout the ablation procedure. Such procedures may require the ablation electrode of the ablation catheter to remain in contact with the ventricular tissue for a period of time well over a minute. This is particularly difficult when the heart is beating, sometimes irregularly, during the entire ablation procedure. Thus, it is critical that the ablation electrode be maintained at the desired location and also be constrained from movement throughout the ablation procedure.

There is generally only one effective approach to the positioning of an ablation catheter in the left ventricle for ablation procedures. This approach is to introduce the catheter into the femoral artery using a standard introducer and advance it up the aorta, across the aortic valve into the left ventricle and then position its electrode adjacent to the wall of the left ventricle which is near the reentry circuits. This is commonly referred to as the "retrograde" approach. The mapping or ablation catheter is then inserted through the guiding introducer into the left ventricle and positioned adjacent to the wall of the left ventricle near the reentry circuits. Specific locations are chosen for the mapping or ablation of the ventricular tissue, including specifically locations on the lateral freewall, posterior freewall, septal wall and anterior freewall.

Mere introduction of the ablation and mapping catheter (10) into the left ventricle for a retrograde approach is not sufficient to effectively and efficiently perform the ablation procedures on the reentry circuits. The medical practitioner commonly monitors the introduction of the catheter (10) and its progress through the vascular system by a fluoroscope. Such fluoroscopes can not easily identify the specific features of the heart in general, and the critically important structures of the left ventricle in specific, thus making placement of the ablation electrode difficult. This placement is especially difficult as the beating heart is in motion. In addition, the catheter (10) will be moving within the left ventricle as blood is being pumped through the heart throughout the procedure. The guiding introducers (20) of the instant invention address and solve these problems.

Referring now to FIGS. 2 through 5, the guiding introducer of the present invention for use in the left ventricle for the treatment of VT is comprised of first, (22) second (24) and third (26) sections. (Each section is preferably formed as an integral portion of the entire guiding introducer (20) without discrete divisions. However, the division of the guiding introducer into three different sections better illustrates the overall shape of the guiding introducers.) Each of the guiding introducers (20) will be shown in either two or three views. In each of the views for ease of analysis, the guiding introducer (20) will be secured to a valve for attachment to a conventional side port tubing and stop cock. In each such arrangement, the shape of the guiding introducer (20) and each of its sections will be described, making reference to its position in relation to the side port and side port tubing where the proximal end of the guiding introducer (20) is secured to the side port tubing. In the first referenced figure of each embodiment (FIGS. 2A, 3A, 4A and 5A), the side port tubing is generally viewed as if it is behind the first section (22) of the guiding introducer (20). The remaining drawings of each embodiment will show the guiding introducer (20) after rotation of the guiding introducer (20) about the axis of one of the sections of the guiding introducer (20). Each will focus upon the curved portions of the second (24) and third (26) sections. In particular, each will focus on the curved portion of the third section and the (22, 24) extent it is curved away from the plane of the first two sections when viewed from the side of the guiding introducer (20), such that the first and second sections are merged into a single plane as shown in FIGS. 2B, 3B, 4B and 5B.

The first section (22) in each embodiment of the guiding introducers (20) is the same general shape. The first section (22) is a conventional, generally elongated hollow, straight introducer section (22) of sufficient length for introduction into the patient and for manipulation from the point of insertion to the specific desired location within the heart. (The overall length of the first section as shown in the drawings has been reduced for ease of viewing.)

Merged with the distal end of the first section of the guiding introducer (20) is the second section (24) which is a smooth, generally flat curve, curving to the left as shown in FIGS. 2A, 3A, 4A and 5A. The extent of the curve of this second section (24) is the same in the guiding introducers

Figures 2A, 2B:
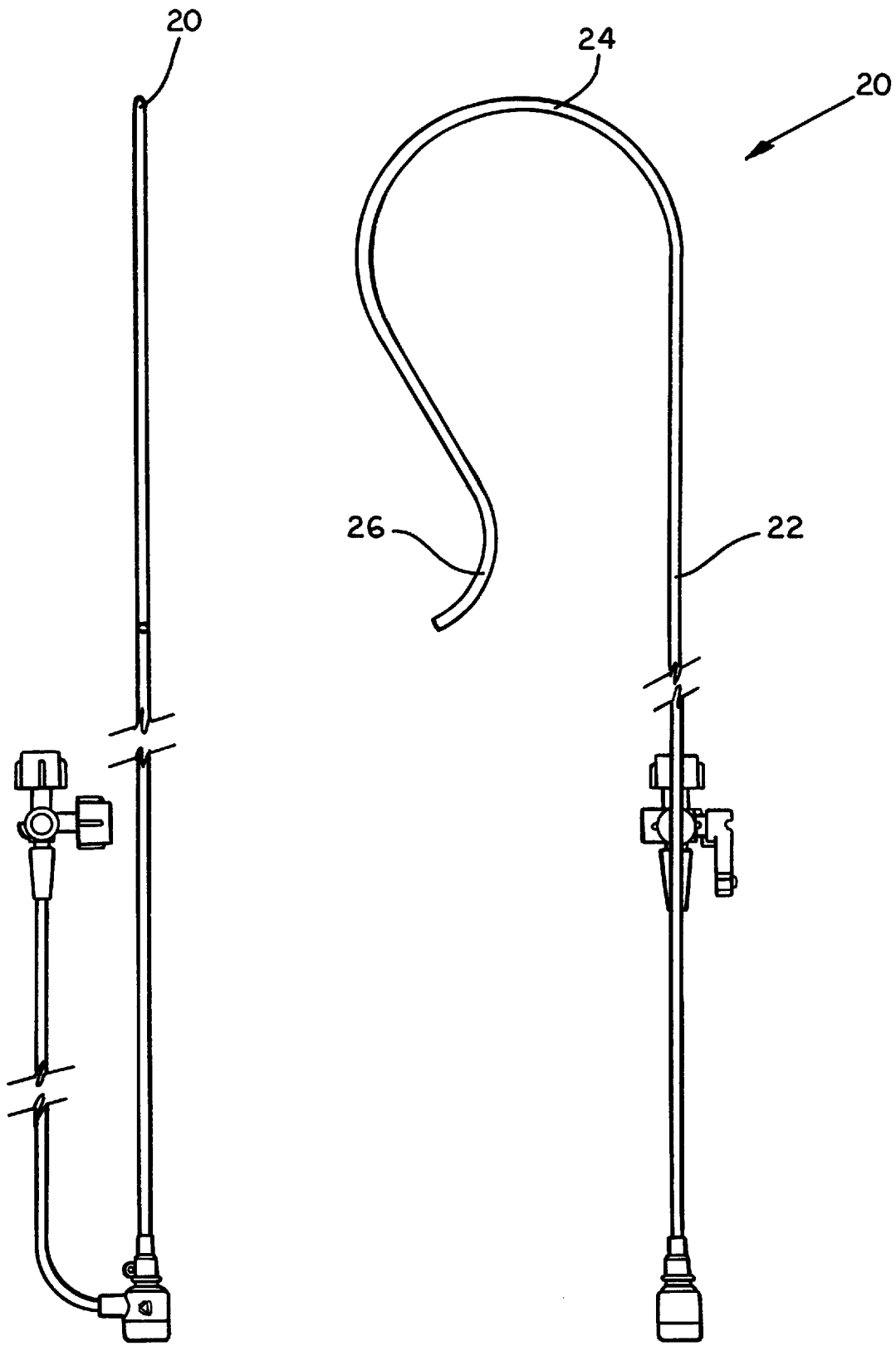
FIG. 2A is a side view of the first embodiment of the guiding introducer for treatment of ventricular tachycardia wherein the site for treatment in the left ventricle is on the septal wall, such that the side port tubing attached to the proximal end of the guiding introducer is located directly behind the first section of the guiding introducer.
FIG. 2B is a side view of the first embodiment of the guiding introducer rotated 90° clockwise from the position of FIG. 2A, when viewed from the perspective of the proximal end of the guiding introducer, such that the side port is directed to the left of the guiding introducer.
Figures 4A, 4B:
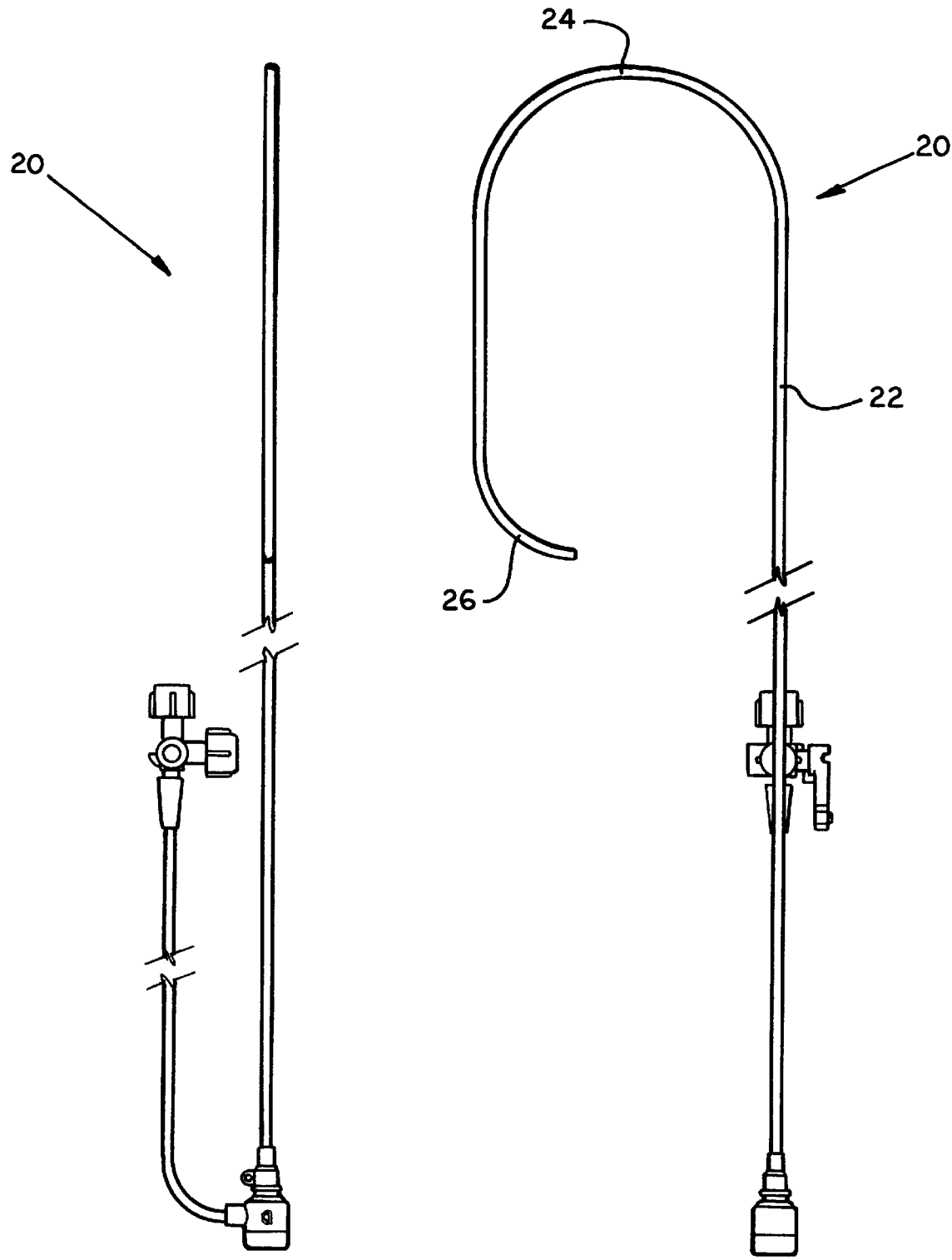
FIG. 4A is a side view of the third embodiment of the guiding introducer for treatment of ventricular tachycardia, wherein the site for treatment in the left ventricle is on the lateral freewall, such that the side port tubing attached to the proximal end of the guiding introducer is located directly behind the first section of the guiding introducer.
FIG. 4B is a side view of the third embodiment of the guiding introducer rotated 90° clockwise from the position of FIG. 4A, when viewed from the perspective of the proximal end of the guiding introducer, such that the side port is directed to the left of the guiding introducer.

(20) of FIGS. 2A and 3A and also the same in FIGS. 4A and 5A. However, the extent of the curve in FIGS. 2A and 3A is greater than the curve shown in FIGS. 4A and 5A. The curve of FIGS. 2A and 3A has a radius of from about 1.0 in. to about 2.0 in. and preferably from about 1.3 in. to about 1.7 in. The extent of the arc of the curve is from about 190 to about 230 degrees and preferably from about 200 to about 220 degrees of arc. The curve of the second section of the guiding introducer (20) as shown in FIGS. 4A and 5A also has a radius of from about 1.0 in. to about 2.0 in. and preferably from about 1.3 in. to about 1.7 in. However, the extent of the arc of the curve as shown in FIGS. 4A and 5A is reduced from that in FIGS. 2A and 3A from about 160 to about 200 degrees and preferably from about 170 to about 190 degrees of arc. The first (22) and second (24) sections of each of the four guiding introducers (20) are generally coplanar (within about 15 degrees of coplanar).

Figure 1B:
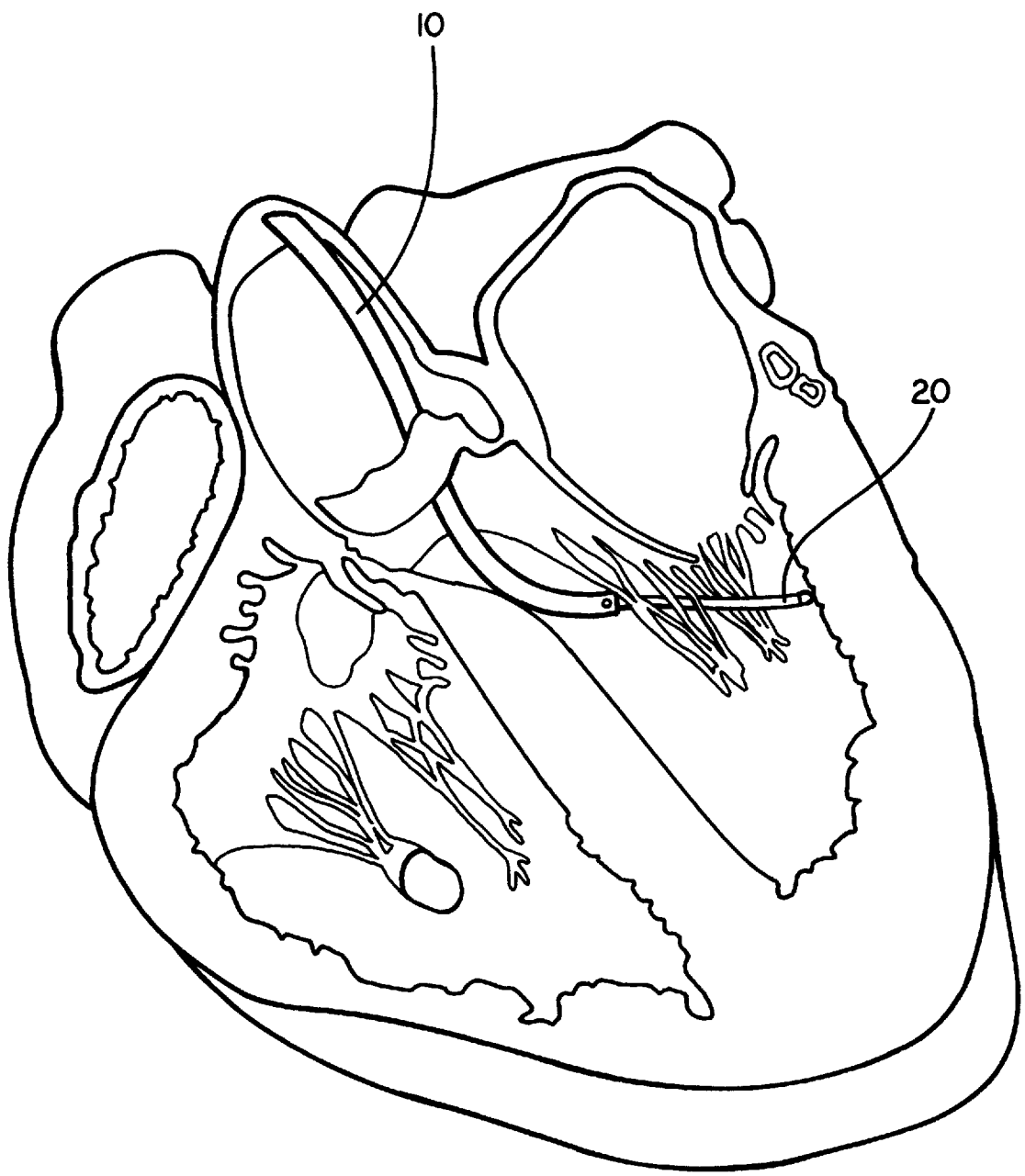
FIG. 1B is a cut away view of the heart showing a retrograde guiding introducer for ablation procedures on the left ventricular lateral wall.

The third section of each guiding introducer (20) is merged with the distal end of the second section (24) of each guiding introducer (20). The structure of the third section (26) of the guiding introducer (20) will depend on the location in the left ventricle being treated. As previously stated, the guiding introducers (20) are used to place a mapping or ablating catheter (10) in a precise position in the left ventricle for treatment of VT by application of an ablation and mapping catheter to the septal wall, anterior freewall, lateral freewall or posterior freewall. (See, for example, FIGS. 1A and 1B.) To accomplish these procedures, the third section (26) is comprised of a generally straight portion merged with a curved portion. The straight portion of the first two embodiments as shown in FIGS. 2A and 3A, is from about 1.0 in. to about 2.5 in. in length and preferably from about 1.5 to about 2.0 in. length. The straight portion of the third section (26) of the third and fourth embodiments of the guiding introducers (20) as shown in FIGS. 4A and 5A is from about 2.0 in. to about 3.0 in. and preferably from about 2.5 in. to about 3.0 in. in length. In all four embodiments, the straight portion is generally coplanar with the first (22) and second (24) sections (within about 15 degrees of coplanar).

In the first embodiment the curved portion of the third section (26) curves to the left (as shown in FIG. 2A) away from the first section, in a smooth curve with a radius of about 0.5 to about 1.5 in. and preferably about 0.8 to about 1.2 in. This curved portion curves in an arc from about 70 to about 110 degrees and preferably from about 80 to about 100 degrees of arc away from the straight portion as shown in FIG. 2A. This curved portion may also curve out of plane with the first and second sections from about 45 degrees clockwise to about 45 degrees counterclockwise when viewed from the proximal end of the first section (22). By adjusting the extent of the curve of the curved portion of the third section (26) out of plane with the first and second sections, the guiding introducer (20) can direct the ablation catheter (10) to cover a significant portion of the wall of the left ventricle. This curved portion extends about 0.6 to about 1.5 in. away from the straight section and preferably about 0.8 to about 1.2 in. away from the straight section. This first embodiment is designed for use in the treatment of tachycardia on the septal wall of the left ventricle, sometimes referred to as Belhassen Tachycardia. See FIG. 1A.

The distal tip of all of the guiding introducers (20) may be, and preferably will be, tapered to form a good transition with a dilator. This tapering is preferably less than 10° and more preferably about 4° to about 7°. The guiding introducers (20) preferably may also contain one or a multitude of radiopaque tip marker bands near the distal tip of the guiding introducer (20). These guiding introducers (20) also preferably contain one or a plurality of vents near the distal tip of the guiding introducer (20), preferably three or four such vents. The vents are preferably located no more than about 1.00 in. from the tip of the guiding introducer (20) and more preferably 0.10 to about 1.00 in. from the tip. The size of these vents should be in the range of about 40 to about $60/1000$ of an inch in diameter. These vents are generally designed to prevent air from entering the guiding introducer caused by the withdrawal of the catheter (10) contained within the guiding introducer (20) in the event the distal end of the guiding introducer (20) is occluded. For example, if the tip of the guiding introducer (20) is placed against the myocardium and the catheter (10) located within the guiding introducer (20) is withdrawn, a vacuum may be created within the guiding introducer if no vents are provided. If such vacuum is formed, air may be forced back into the guiding introducer (20) by the reintroduction of a catheter (10) into the lumen of the guiding introducer (20). Such air could cause significant problems in the patient, including the possibility of a stroke, heart attack or other such problems common with air embolisms. The addition of vents near the distal tip of the guiding introducer (20) prevents the formation of such vacuum by permitting fluid, presumably blood, to be drawn into the lumen of the guiding introducer (20) as the catheter is being removed from the guiding introducer (20), thus preventing air from entering the guiding introducer (20).

The guiding introducers (20) may be made of any material suitable for use in humans which has a memory or permits distortion from, and substantial return to, the desired three dimensional or complex multiplanar shape. For the purpose of illustration and not limitation, the internal diameter of the guiding introducer (20) may vary from about 6 to about 10 "French" (1 French equals $\frac{1}{3}$ of a millimeter). Such guiding introducer (20) can accept dilators from about 6 to about 10 French and appropriate guidewires. Obviously, if larger or smaller dilators or catheters are used in conjunction with the guiding introducers (20) of the instant invention, modifications in size or shape can be made to the instant guiding introducers (20). Variations in size and shape of the guiding introducers (20) are also intended to encompass pediatric uses, although the preferred uses are for adult human hearts. It is well recognized that pediatric uses may require reductions in size of the various sections of the guiding introducer (20), in particular the first section (20), but without any significant modification to the shape or curves of the guiding introducer (20).

In addition, variations in size or shape of the guiding introducers (20) are also intended to encompass the specialized situations that sometimes occur in patients with enlarged and rotated hearts.

The second embodiment of the guiding introducer (20) (FIGS. 3A, 3B and 3C) is designed for use in the treatment of left ventricular tachycardia located on the anterior freewall of the left ventricle. In this embodiment, the first and second sections and the straight portion of third section are the same as previously discussed in the description of the first embodiment. The difference in shape is the curved portion of the third section (26). The curve of the curved portion is similar in shape to the curved portion of the first embodiment. It curves away from the straight portion in a smooth curve with a radius of from about 0.7 to about 1.3 in. and preferably from about 0.9 to about 1.1 in. The arc of this curved portion is preferably from about 70 to about 110 degrees and more preferably from about 80 to about 100 degrees. The distance from the straight portion of the third section (26) to the distal tip of the guiding introducer (20) is preferably from about 0.8 to about 1.2 in. and more preferably from about 0.9 to about 1.1 in. ending in the distal tip. In this second embodiment, the curved portion of the third section (26) curves out of the plane formed by the first and second sections clockwise from about 45 degrees to about 135 degrees when viewed from the proximal end of the first section (22). See FIG. 3C.

The third embodiment of the guiding introducer (20) (FIGS. 4A and 4B) is designed for use in the treatment of left ventricular tachycardia located on the lateral freewall of the left ventricle. See FIG. 1B. The shape of this guiding catheter (10) varies from the first and second embodiment in the extent of the curvature of the second section (24) and also the shape of the curved portion of the third section (26). The first section (22) of this third embodiment is generally the same as disclosed in the first and second embodiments. As previously discussed, the extent of the curvature of the second section (24) of this third embodiment is less than the curvature of the second section (24) of the first and second embodiments. (Compare FIG. 4A with FIGS. 2A and 3A.) The extent of the curvature of this second section (24) is preferably from about 160 to about 200 degrees and more preferably from about 170 to about 190 degrees of arc. The second section is generally coplanar with the first section (22). See FIG. 4B.

The third section (24) of the third embodiment has a straight portion and a curved portion. The straight portion of the third section (26) of the third embodiment has been previously discussed and is generally coplanar with the first (22) and second (24) sections. The curved portion of the third section begins at the distal end of the straight portion of the third section (26). The curved portion of the third section (26) is similar to the curved portion of the first embodiment except it is curved in a simple curve in the opposite direction of the first embodiment, to the right (as shown in FIG. 4A). The extent of the curve is similar to the extent of curvature of the curved portions of the first (22) and second (24) embodiments. (Compare FIGS. 2A and 3C with FIG. 4A.) The arc of the curve is from about 70 to about 110 degrees and preferably from about 80 to about 100 degrees. The radius of this curve is from about 0.7 in. to about 1.3 in. and preferably from about 0.9 in. to about 1.1 in. As with the curved portion of the first embodiment, the curved portion of the third section (26) can curve out of the plane formed by the first and second section from about 45 degrees clockwise to about 45 degrees counterclockwise when viewed from the proximal end of the first section (22).

The fourth embodiment of the guiding introducer (20) (FIGS. 5A, 5B and 5C) is designed for use in the treatment of left ventricular tachycardia located on the posterior freewall of the left ventricle. The first, second and straight portion of the third section (26) are the same as disclosed in the third embodiment and are substantially coplanar. (Compare FIGS. 4A and 5A) The curved portion of the third section (26) is comprised of a simple curved section, curving to the left as shown on FIG. 5B or upward as shown in FIG. 5C. The arc of the curve is from about 70 to about 110 degrees and preferably 80 to about 100 degrees. The radius of this curve is from about 0.7 in. to about 1.3 in. and preferably from about 0.9 in. to about 1.1 in. As with the curved portion of the first, second and third embodiments, the curved portion of the third section (26) of the fourth embodiment can be rotated out of the plane formed by the first (22) and second (24) sections from about 45 degrees to about 135 degrees counterclockwise when viewed from the proximal end of the first section (22). See FIG. 5C.

As a result of these four embodiments, four separate guiding introducers (20) are disclosed which are similar in shape except for the angle of the curve of the second section (24), the length of the straight portion of the third section (26), the direction of curve of the curved portion and the extent of rotation of this curved portion of the third section out of the plane formed by the first (22) and second (24) sections. By each of the four guiding introducers (20) being about to rotate at least about 45 degrees clockwise and counterclockwise from the fixed position shown in the respective Figures (for example FIGS. 3C and 5C), a full 360 degrees of rotation is possible about the plane formed by the first and second sections with these guiding introducers (20) thereby assisting in ablation procedures on all walls of the left ventricle from septum to anterior to lateral to posterior freewall.

In operation, a modified Seldinger technique is normally used for the insertion of the catheter (10) into the femoral artery. Using this procedure, a small skin incision is made at the appropriate location to facilitate the catheter (10) or dilator passage. The subcutaneous tissue is then dissected, followed by a puncture of the vessel with an appropriate needle with stylet positioned at a relatively shallow angle. The needle is then partially withdrawn and reinserted at a slightly different angle into the vessel, making sure that the needle remains within the vessel. A soft flexible tip of an appropriately sized guidewire is then inserted through and a short distance beyond the needle into the vessel. Firmly holding the guidewire in place, the needle is removed. The guidewire is then advanced through the artery up to the aorta, across the aortic valve into the left ventricle. With the guidewire in place, a dilator is then placed over the guidewire with the guiding introducer (20) placed over the dilator. The dilator and guiding introducer (20) generally form an assembly to be advanced together along the guidewire into the left ventricle. After insertion of the assembly, the guidewire and dilator are then withdrawn. The catheter (10) to be used for treatment of left ventricular tachycardia is advanced through the lumen of the guiding introducer (20) and is placed at an appropriate location in the left ventricle. The choice of the guiding introducer (20) to be used will depend on the location of the tachycardia in the left ventricle as has previously been discussed.

By choice of the desired predetermined shape of the guiding introducer in conjunction with fluoroscopic viewing, the distal portion of the guiding introducer (20) can be manipulated to direct the distal end of an ablation and/or mapping catheter (10) placed within the lumen of the guiding introducer (20), to a specific internal surface within the left ventricle. In addition, by providing sufficient rigidity and support as the guiding introducer (20) is held in place by the anatomical structure of the heart as well as the vasculature, the distal end of the guiding introducer (20) can be maintained in that fixed location or surface position of the endocardial structure to permit the appropriate procedures to be performed. If sensing procedures are involved, the guiding introducer (20) is placed in the desired location. At that point, the electrical activity of the heart peculiar to that location can be precisely determined by use of a sensing electrophysiology catheter placed within the guiding introducer (20). Further, as the guiding introducer permits precise location of catheters (10), the ablation electrode of an ablation catheter (10) may be placed at a precise location for destruction by the use of energy, for example, thermal, laser, direct current (low energy direct current, high energy direct current or fulgutronization procedures), possibly along with reduced temperature or iced procedures.

This precise location of the ablation catheter electrode is important as there will be no dilution of the energy delivered due to unfocused energy being dissipated over the entire cardiac chamber and lost in the circulating blood by a constantly moving tip of the ablating catheter (10). This permits a significantly reduced amount of energy to be applied while still achieving efficient ablation. Further, time used to perform the procedure is significantly reduced over procedures where no guiding introducer is used. The precise placement of the ablation catheter (10) within the left ventricle is particularly important because of the difficulties associated with the ablation of left ventricular tachycardia. Treatment of tachycardia in the left ventricle is significantly more difficult because of the thickness of the wall of the left ventricle than, for example, the treatment of Wolff-Parkinson-White Syndrome where the ablation procedures occur in a portion of the heart where the myocardial tissue is significantly thinner. It has been determined that the time of ablation must be substantially lengthened to achieve not only two dimensional ablation but also the three dimensional ablation that is necessary for the ablation of left ventricular tissue. Thus, not only is the precise location of the ablation electrode necessary, but continuous contact of the ablation electrode with the left ventricle is also necessary. Larger or longer electrodes of the ablation catheter (10) may be necessary to achieve efficient and effective ablation. Further, other types of energy than radio frequency may be necessary for the extensive ablation necessary for the elimination of the location within the ventricle.

It will be apparent from the foregoing that while particular forms of the invention have been illustrated and described, various modifications can be made without departing from the spirit and scope of the invention. Accordingly, it is not intended that this invention be limited except as by the appended claims.

It is claimed:

1. A precurved, cardiac chamber guiding introducer for use with an ablation catheter for the treatment of ventricular tachycardia in the left ventricle of the heart, comprising an elongate tube having a lumen extending from a proximal to a distal end, wherein the tube comprises first, second and third sections, wherein a portion of the tube is formed in a predetermined, curved shape that conforms to an anatomy of the left ventricle of the heart, wherein the second section is a curved section comprised of a generally flat curve with a radius of about 1.0 in. to about 2.0 in. and an arc of the curve from about 190 to about 230 degrees.

2. The guiding introducer of claim 1 wherein the third section is comprised of a straight portion and a curved portion.

3. The guiding introducer of claim 2 wherein the straight portion of the third section is from about 1.0 in. to about 2.5 in. in length and the curved portion is a curve with a radius of about 0.5 to about 1.5 in. and an arc of about 70 to about 110 degrees, wherein the curve is within about 45 degrees of being in a plane formed by the first and second sections, and wherein the curve is directed generally away from the first section of the guiding introducer.

4. The guiding introducer of claim 2 wherein the straight portion of the third section is from about 2.0 to about 2.5 in. in length and the curved portion is a curve with a radius of about 0.5 to about 1.5 in. and an arc of about 70 to about 110 degrees, and wherein such curve is curved clockwise out of a plane formed by the first and second sections about 45 to about 135 degrees.

5. A precurved, cardiac chamber guiding introducer for use with an ablation catheter for the treatment of ventricular tachycardia in the left ventricle of the heart, comprising an elongate tube having a lumen extending from a proximal to a distal end, wherein the tube comprises first, second and third sections, wherein a portion of the tube is formed in a predetermined, curved shape that conforms to an anatomy of the left ventricle of the heart, wherein the second section is a curved section comprised of a generally flat curve with a radius of about 1.0 in. to about 2.0 in. and an arc of the curve from about 160 to about 200 degrees.

6. The guiding introducer of claim 5 wherein the third section is comprised of a straight portion and a curved portion.

7. The guiding introducer of claim 6 wherein the straight portion of the third section is from about 2.0 to about 3.0 in. in length and the curved portion of the third section is a curve with a radius of about 0.5 to about 1.5 in. and an arc of about 70 to about 110 degrees, wherein said curve is within about 45 degrees of being in a plane formed by the first and second sections and wherein the curve is directed generally toward the first section of the guiding introducer.

8. The guiding introducer of claim 6 wherein the straight portion of the third section is from about 2.0 to about 3.0 in. in length and the curved portion is a curve with a radius of about 0.5 to about 1.5 in. and an arc of about 70 to about 110 degrees, and wherein said curve is curved counterclockwise out of a plane formed by the first and second sections about 45 to about 135 degrees.

* * * * *